(12) United States Patent  
Bhethanabotla et al.

(10) Patent No.: US 9,005,890 B1  
(45) Date of Patent: Apr. 14, 2015

(54) ALLOY NANOPARTICLES FOR METAL-ENHANCED LUMINESCENCE

(75) Inventors: Venkat R. Bhethanabotla, Tampa, FL (US); Sanchari Chowdhury, Tampa, FL (US)

(73) Assignee: University of South Florida, Tampa, FL (US)

( * ) Notice: Subject to any disclaimer, the term of this patent is extended or adjusted under 35 U.S.C. 154(b) by 969 days.

(21) Appl. No.: 12/549,684

(22) Filed: Aug. 28, 2009

Related U.S. Application Data

(60) Provisional application No. 61/092,564, filed on Aug. 28, 2008.

(51) Int. Cl.  
*C12Q 1/68* (2006.01)

(52) U.S. Cl.  
CPC .......... *C12Q 1/68* (2013.01); *C12Q 2563/149* (2013.01)

(58) Field of Classification Search  
USPC .................................. 424/401; 435/6.11, 7.1  
IPC ......... B01L 2300/0864,2400/0406, 7/52; B82Y 15/00; A61L 2/082; C12Q 1/68, 2563/149  
See application file for complete search history.

(56) References Cited

U.S. PATENT DOCUMENTS

| | | |
|---|---|---|
| 2003/0228682 A1 | 12/2003 | Lakowicz et al. |
| 2004/0157237 A1 | 8/2004 | Malak et al. |
| 2005/0142605 A1* | 6/2005 | Malak ............... 435/6 |
| 2007/0269826 A1 | 11/2007 | Geddes |
| 2009/0022766 A1* | 1/2009 | Geddes .......... 424/401 |
| 2010/0280098 A1* | 11/2010 | Juliano et al. ........ 514/44 A |

OTHER PUBLICATIONS

Hirai et al. (Wavelength tuning of surface plasmon resonance by annealing silver-copper nanoparticles, Journal of Applied Physics 100, 014309 (2006)).*

A. K. Sharma et al 2008. "On the Performance of Surface Plasmon Resonance Based Fibre Optic Sensor with Different Bimetallic Nanoparticle Alloy Combinations." J. Phys. D: Appl. Phys. vol. 41. pp. 1-7.

S. A. Zynio et al. 2002. "Bimetallic Layers Increase Sensitivity of Affinity Sensors Based on Surface Plasmon Resonance." Sensors. vol. 2. pp. 62-70.

K. Ray et al. 2007. "Aluminum Nanostructured Films as Substrates for Enhanced Fluorescence in the Ultraviolet-Blue Spectral Region." Anal. Chem. vol. 79. pp. 6480-6487.

J. Zhang et al. 2005. "Metal-Enhanced Fluoroimmunoassay on a Silver Film by Vapor Deposition." J. Phys. Chem. B. vol. 109. pp. 7969-7975.

(Continued)

*Primary Examiner* — Weiping Zhu  
(74) *Attorney, Agent, or Firm* — Michele L. Lawson; Smith & Hopen, P.A.

(57) ABSTRACT

Metal enhanced luminescence using alloy nanoparticles offers additional degrees of freedom for tuning their optical properties by altering atomic composition and atomic arrangement when compared to pure metal nanoparticles such as gold and silver. Surface plasmon resonance wavelengths of silver-copper nanoparticles were tuned in the visible and near infrared region by changing annealing temperature. Strong emission enhancement of luminophores at the vicinity of the Ag—Cu nanoparticles was shown when the SPR spectrum was tuned to produce maximum spectral overlap. As the SPR spectrum can be easily tailored, this platform can be effectively used to enhance luminescence of different luminophores.

15 Claims, 6 Drawing Sheets

(56) References Cited

OTHER PUBLICATIONS

K. Aslan et al. 2006. "Microwave-Accelerated Metal-Enhanced Fluorescence (MAMEF): Application to Ultra Fast and Sensitive Clinical Assays." Journal of Fluorescence. vol. 16. No. 1. pp. 3-8.

M. H. Chowdhury et al. 2007. "Metal-Enhanced Fluorescence of Phycobiliproteins from Heterogeneous Plasmonic Nanostructures." J. Phys. Chem. C Nanomater Interfaces. vol. 111. No. 51. pp. 18856-18863.

J. Zhang et al. 2006. "Metal-Enhanced Fluorescence of an organic Fluorophore Using Gold Particles." Optical Society of America.

A. Pal et al. 2007. "Preparation of Silver, Gold and Silver-Gold Bimetallic Nanoparticles in w/o Microemulsion Containing TritonX-100." Colloids and Surfaces A: Physicochem. Eng. Aspects. vol. 302. pp. 483-487.

J. Zhu. 2005. "Theoretical Study of the Optical Absorption Properties of Au—Ag Bimetallic Nanospheres." Physica E. vol. 27. pp. 296-301.

E. Matveeva et al. 2004. "Metal-Enhanced Fluorescence Immunoassays Using Total Internal Reflection and Silver Island-Coated Surfaces." Analytical Biochemistry. vol. 334. pp. 303-311.

J. Zhang et al. 2007. "Preparation and Optical Properties of Silica@Ag—Cu Alloy Core-Shell Composite Colloids." Journal of Solid State Chemistry. vol. 180. pp. 1291-1297.

E. Dulkeith et al. 2005. "Gold Nanoparticles Quench Fluorescence by Phase Induced Radiative Rate Suppression." Nano Letters. vol. 5. No. 4. pp. 585-589.

J. R. Lakowicz et al. 2002. "Radiative Decay Engineering." Analytical Biochemistry. vol. 301. pp. 261-277.

J. Malicka et al. 2003. "Effects of Fluorophore-to-Silver Distance on the Emission of Cyanine-Dye-Labeled Oligonucleotides." Analytical Biochemistry. vol. 315. pp. 57-66.

F. Tam et al. 2007. "Plasmonic Enhancement of Molecular Fluorescence." Nano Letters. vol. 7. No. 2. pp. 496-501.

K. Aslan et al. 2007. "Metal-Enhanced Fluorescence from Gold Surfaces: Angular Dependent Emission." J Fluoresc. vol. 17. pp. 7-13.

P. P. Pompa et al. 2006. "Metal-Enhanced Fluorescence of Colloidal Nanocrystals with Nanoscale Control." Nature Nanotechnology. vol. 1. pp. 126-130.

Y. Chen et al. 2007. "Dependence of Fluorescence Intensity on the Spectral Overlap Between Fluorophores and Plasmon Resonant Single Silver Nanoparticles." Nano Letters. vol. 7. No. 3. pp. 690-696.

M. Thomas et al. 2004. "Single-Molecule Spontaneous Emission Close to Absorbing Nanostructures." Applied Physics Letters. vol. 85. No. 17. pp. 3863-3865.

J. Song et al. 2002. "Fabrication and Optical Properties of Metastable Cu—Ag Alloys." Applied Optics. vol. 41. No. 25. pp. 5413-5416.

M. Hirai et al. 2006. "Wavelength Tuning of Surface Plasmon Resonance by Annealing Silver-Copper Nanoparticles." Journal of Applied Physics. vol. 100. pp. 014309-1-014309-4.

M. Hirai et al. 2007. "Optical Properties and Microstructure of Silver-Copper Nanoparticles Synthesized by Pulsed Laser Deposition." Journal of Electronic Materials. vol. 36. No. 12. pp. 1574-1578.

M. Moskovits et al. 2002. "Bimetallic Ag—Au Nanoparticles: Extracting Meaningful Optical Constants from the Surface-Plasmon Extinction Spectrum." Journal of Chemical Physics. vol. 116. No. 23. pp. 10435-10446.

J. Azoulay et al. 2000. "Quenching and Enhancement of Single-Molecule Fluorescence Under Metallic and Dielectric Tips." Europhysics Letters. vol. 51. No. 4. pp. 374-380.

C. D. Geddes et al. 2003. "Photodeposition of Silver Can Result in Metal-Enhanced Fluorescence." Applied Spectroscopy. vol. 57. No. 5. pp. 526-531.

J. R. Lakowicz et al. 2003. "Radiative Decay Engineering: The Role of Photonic Mode Density in Biotechnology." Journal of Physics D: Applied Physics. vol. 36. pp. R240-R249.

K. Ray et al. 2006. "Metal-Enhanced Fluorescence from CdTe Nanocrystals: A Single-Molecule Fluorescence Study." J. Am. Chem. Soc. vol. 128. pp. 8998-8999.

K. Ray et al. 2006. "Distance-Dependent Metal-Enhanced Fluorescence from Langmuir-Blodgett Monolayers of Alkyl-NBD Derivatives on Silver Island Films." Langmuir. vol. 22. pp. 8374-8378.

Y. Zhang et al. 2007. "Metal-Enhanced Fluorescence from Copper Substrates." Applied Physics Letters. vol. 90. pp. 173116-1-173116-3.

C. D. Geddes et al. 2003. "Silver Fractal-Like Structures for Metal-Enhanced Fluorescence: Enhanced Fluorescence Intensifies Probe Photostabilities." Journal of Fluorescence. vol. 13. No. 3. pp. 267-276.

K. Aslan et al. 2005. "Nanogold Plasmon Resonance-Based Glucose Sensing. 2. Wavelength-Ratiometric Resonance Light Scattering." Anal. Chem. vol. 77. pp. 2007-2014.

K. Aslan et al. 2005. "Enhanced Ratiometric PH Sensing Using SNAFL-2 on Silver Island Films: Metal-Enhanced Fluorescence Sensing." Journal of Fluorescence. vol. 15. No. 1. pp. 37-40.

K. Aslan et al. 2007. "Fluorescent Core-Shell Ag©SiO2 Nanocomposites for Metal-Enhanced Fluorescence and Single Nanoparticle Sensing Platforms." J. Am. Chem. Soc. vol. 129. pp. 1524-1525.

M. H. Chowdhury et al. 2006. "Metal-Enhanced Chemiluminescence." J Fluoresc. vol. 16. pp. 295-299.

C. D. Geddes et al. 2002. "Metal-Enhanced Fluorescence." Journal of Fluorescence. vol. 12. No. 2. pp. 121-129.

Aslan, K. et al. 2005. "Fast and Slow Deposition of Silver Nanorods on Planar Surfaces: Application to Metal-Enhanced Fluorescence." J. Phys. Chem. B. vol. 109. pp. 3157-3162.

Aslan, K et al. 2005. "Metal-Enhanced Fluorescence Using Anisotropic Silver Nanostructures: Critical Progress to Date." Anal. Bioanal. Chem. vol. 382. pp. 926-933.

Geddes, C. D. et al. 2003. "Metal-Enhanced Fluorescence (MEF) Due to Silver Colloids on a Planar Surface: Potential Applications of Indocyanine Green to in Vivo Imaging." J. Phys. Chem. A. vol. 107. pp. 3443-3449.

Ray, K. et al. 2006. "Langmuir-Blodgett Monolayers of Long-Chain NBD Derivatives on Silver Island Films: Well-Organized Probe Layer for the Metal-Enhanced Fluorescence Studies." J. Phys. Chem. B. vol. 110. pp. 13499-13507.

Zhang, J. et al. 2007. "Emission Behavior of Fluorescently Labeled Silver Nanoshell: Enhanced Self-Quenching by Metal Nanostructure." J. Phys Chem. C. vol. 111. pp. 1955-1961.

Kummerlen, J. et al. 1993. "Enhanced Dye Fluorescence Over Silver Island Films: Analysis of the Distance Dependence." Molecular Physics. vol. 80. No. 5. pp. 1031-1046.

Tarcha, P. J. et al. 1999. "Surface-Enhanced Fluorescence on SiO2-Coated Silver Island Films." Applied Spectroscopy. vol. 53. No. 1. pp. 43-48.

Link, S. et al. 1999. "Alloy Formation of Gold-Silver Nanoparticles and the Dependence of the Plasmon Absorption on Their Composition." J. Phys. Chem. B. vol. 103. pp. 3529-3533.

Xin Li, et al., Flourescence quenching of quantum dots by gold nanorods and its application to DNA detection. Applied Physics Letters, 94, (2009).

Shengliang Li, et al., Delivery of Quantum Dot-siRNA Nanoplexes in SK-N-SH Cells for BACE1 Gene Silencing and Intracellular Imaging. Molecular Therapy-Nucleic Acids (2012) 1, e20.

Julien R. G. Navarro, et al., Supporting information for Resonant light scattering spectroscopy of gold, silver and gold-silver alloy nanoparticles and optical detection in microfluidic channels. Electronic Supplementary Material (ESI) for Analyst. The Royal Society of Chemistry, 2013, pp. 1-18.

(56) References Cited

OTHER PUBLICATIONS

Julien R. G. Navarro, et al., Resonant light scattering spectroscopy of gold, silver and gold-silver alloy nanoparticles and optical detection in microfluidic channels. Analyst, 2013, 138, 583.

Prashant K. Jain, et al., Calculated Absorption and Scattering Properties of Gold Nanoparticles of Different Size, Shape, and Composition: Applications in Biological Imaging and Biomedicine. J. Phys. Chem. B (2006), 110, 7238-7248.

Yugang Sun, et al., Gold and silver nanoparticles: A class of chromophores with colors tunable in the range from 400 to 750 mm. Analyst, 2003, 128, 686-691.

E. Dulkeith, et al., Flourescence Quenching of Dye Molecules near Gold Nanoparticles: Radiative and Nonradiative Effects. Physical Review Letters, vol. 89, No. 20, Nov. 11, 2002, pp. 203002-1-4.

Ignacio Vaya, et al., Fluorescence of Natural DNA: Form the Femtosecond to the Nanosecond Time Scales. J. Am. Chem. Soc. 2010, 132, 11834-11835.

\* cited by examiner

A

B

C

ALLOY NANOPARTICLES FOR METAL-ENHANCED LUMINESCENCE

CROSS REFERENCE TO RELATED APPLICATIONS

This application claims priority to U.S. Provisional Patent Application 61/092,564, entitled "Alloy Nanoparticles for Metal-Enhanced Luminescence", filed Aug. 28, 2008, the contents of which are herein incorporated by reference.

STATEMENT OF GOVERNMENT INTEREST

This invention was made with Government support under Grant No. CMS-409401 awarded by the National Science Foundation. The Government has certain rights in the invention.

FIELD OF INVENTION

This invention relates to luminophores. More specifically, this invention relates to alloy nanoparticles for the metal-enhanced luminescence of luminophores.

BACKGROUND OF THE INVENTION

Luminescence based measurements and devices are currently widely used methods in different fields such as biology, chemistry, materials science and medicine. Strong luminescence intensity is one of the most important desired properties of luminophores for these applications, especially in luminescence sensors. There is a continuing need for increasing luminescence sensitivity in biological research. However, detection and sensitivity in general is limited by the luminescence quantum yield and photostability of the probe. It is possible to design and synthesize luminophores with desired spectral properties. However, it is difficult to design luminophores with desired luminescence intensity.

Nearby conducting metallic particles, colloids, and surfaces are known to significantly influence the emission of vicinal luminophores.[5-34] A luminophore near the metal surface is strongly quenched by the metallic surface but is enhanced when it is beyond the quenching region. This enhancement depends on the increase of the intrinsic decay rate of the luminophore, which can be described by lifetime. A reduction in lifetime occurs simultaneously with an increase in intensity. For example, shorter lifetimes for luminophores in proximity to silver nanoparticles coupled with enhanced emission intensities, has been reported in many publications.

Surface plasmon resonance (SPR) wavelength, one of the most important properties of nanostructures, dictates the choice of materials to be used for luminescence enhancement. SPR has been widely used as a quick and accurate detection of various physical, chemical, and biochemical parameters. In SPR, a metal dielectric interface supports an electromagnetic wave called a surface plasmon wave, which is a p=polarized wave that propagates along the interface. When the p-polarized light with a propagation constant equal to that of the surface plasmon wave is incident on such a metal dielectric interface, a strong absorption of light takes place. Surface roughness is known to provide a pathway for the coupling of incident light to surface plasmons and the creation of far-field radiation from the plasmons. Light intensity of nanoparticles at near field is strongly dependent on the SPR wavelength of the metal nanostructures. Spectral overlap between the absorption and emission spectra of luminophore and SPR spectra of metal nanoparticles is very important for optimum luminescence enhancement.

Luminophores in the excited state undergo near-field interactions with the metal nanoparticles to create plasmons. These plasmons radiate away from the nanoparticle to increase luminescence enhancement of luminophores. Excited luminophores that are in close proximity to metal nanoparticles can induce dipoles in the metal nanoparticles which under certain conditions radiate the photophysical properties of the luminophore. The efficiency of luminophore coupling to surface plasmons combined with their high efficiency to radiate produces luminophore-metal systems that display high luminescence quantum yields combined with reduced lifetimes.

Though the phenomena of metal enhanced luminescence (MEL) was originally presented in the 1980s, the demonstration and applications of MEL are largely a new field of investigation. MEL involves the interactions of luminophores with metallic nanoparticles which results in luminescence enhancement, increased photostability, decreased lifetimes due to increased rates of system radiative decay, reduced blinking in single molecule fluorescence spectroscopy, and increased transfer distances for fluorescence resonance energy transfer. The extent of MEL depends on the size, shape and dielectric constant of the nanoparticles which decide the surface plasmon resonance and scattering properties of nanoparticles and also on the separation distance between the metal and the fluorophore.

Luminescence enhancements ranging from tens- to hundreds-fold in signal intensity have been reported in the literature.[4, 6, 8, 12, 14, 25, 35-37] Different applications of metal enhanced luminescence and from different metallic nanoparticles have been reported in recent literature.[8-11, 14, 15, 20, 26, 27, 33, 34, 38]

At the vicinity of conducting metallic nanoparticles such as silver (Ag) and gold (Au), the emission intensity of luminophores is known to be significantly influenced.[1-4, 39, 40] MEL has been studied mostly using silver nanoparticles[5-9, 11-13, 15, 18, 33, 37] due to their intense and narrow SPR peaks. The Ag based sensor is known for its narrow spectral width but is chemically unstable and is highly vulnerable to oxidation when in liquid or gaseous environments. Gold nanoparticles are known to both quench and enhance luminescence depending on the fluorophore-particle separation distance, molecular dipole orientation with respect to particle surface, and size of the nanoparticles.[24,25,41] Relatively smaller (typically less than 30 nm) gold nanoparticles quench fluorescence emission due to non-radiative transfer from the excited states of luminophore molecules to the gold nanoparticles.[41] Larger gold nanoparticles can enhance luminescence due to the increased contribution of nanoparticle scattering.[24,25]

MEL has primarily been studied in the visible —NIR wavelength region given most of the studies have been performed using silver or gold. The problem with this is that many widely used fluorophores absorb or emit at ultraviolet wavelengths. Recently, other metals, such as copper and aluminum, have been reported to enhance luminescence.[28, 34, 39] But, due to the higher ohmic losses, the MEL effect is not as pronounced in Cu and Al as it is in Ag or Au. However, fluorescence does have possibilities to be enhanced in the ultraviolet-blue region of the spectrum using metals such as aluminum and copper. Recently zinc oxide (ZnO) nanorods platforms have been reported to enhance the luminescence intensity significantly, from commonly utilized fluorophores in immunoassays.[36]

Sharma et. al. examined sensitivity, signal-to-noise ratio (SNR), and operating range for different bi-metallic nanoparticles for use in fiber optic SPR based sensors. Specifically they examined gold (Au), silver (Ag), copper (Cu), and aluminum (Al). They found that Cu has a slightly broader SPR curve than Al and its resonance wavelength is longer. Ag follows the same basic pattern and has a broader SPR curve and a higher resonance wavelength than either Cu or Al. Au has the broadest SPR curve and the highest resonance wavelength. They determined that no single metal nanoparticle is able to provide reasonable values for all three performance parameters including sensitivity, SNR and operating range simultaneously. However bi-metallic nanoparticles are able to show significantly high values for these three parameters.[39, 40]

Using nanoparticle platforms, it is possible to increase the quantum yield of weakly luminescent probes by modifying their radiative decay rate to increase their emission efficiency, or by coupling the emission with far field scattering. The emission intensity of luminophores with nearly unit quantum yield can also be improved by enhancing their absorption through increasing the local electric field. The absorption and emission peaks of any luminophore can be predicted by analogy of known luminophores. Light intensity of nanoparticles at near field is strongly dependent on the surface plasmon resonance (SPR) wavelength of the metal nanostructures. SPR wavelength, one of the most important properties of nanostructures, dictates the choice of materials to be used for luminescence enhancement.

Tam et al.[29] found that the enhancement is optimal when the plasmon resonance wavelength of the nanoparticles is tuned to the emission wavelength of the low quantum yield luminophores. The luminescence enhancement is largest when the emission wavelength is slightly red-shifted from that of the plasmon resonance[12]. By tuning the position of the SPR peak of the nanoparticles over a wide range of wavelengths, metal enhanced luminescence (MEL) can be extended to a wide range of luminophores. It appears that the optimal location of the SPR peak of nanoparticles is between the excitation and emission peaks of luminophores for maximum enhancement, as both excitation and emission rates can be enhanced in such a situation.[12]

So far, MEL has been studied mostly on pure metal platforms. SPR wavelengths of pure metal nanoparticles can be tuned to different values by controlling several parameters, such as particle size, shape, particle-to-particle distance and surrounding dielectric medium[12]. However, it is easier to tune SPR spectra of alloy nanoparticles in a wide range of wavelengths as these offer additional degrees of freedom for tuning their optical properties by altering atomic composition and atomic arrangement. This enables development of specifically tailored nanoparticle platforms for MEL of a wide range of luminophores.

The SPR spectrum of Ag is more intense and narrower than that of Cu nanoparticles. The absorption peak attributed to SPR occurs at shorter wavelengths for Ag. Hence by modifying the composition and atomic arrangement we can tune both the breadth and the location of the peak of the SPR spectrum of Ag—Cu alloy nanoparticles. SPR peak wavelengths of Ag—Cu alloy nanoparticles can be tuned easily in the visible and near infrared region by changing only the annealing temperature. We have established simple and straightforward routes for the successful growth and fabrication of nanostructured platforms which can be effectively utilized to enhance the luminescence of any luminophore. We also provide insight into the effect of SPR on MEL. We use theoretical calculations based on models for calculating the excitation enhancement factor by local field effects and the emission enhancement factor due to radiative and nonradiative decay rate change.

The present invention demonstrates that SPR spectra of alloy nanoparticles can easily be tuned by manipulating only one experimental condition to result in maximum spectral overlap of the emission and absorption spectra of the luminophores with the SPR spectrum of the nanoparticles. Specifically we observed enhanced fluorescence emission from two thiol-reactive dyes, Alexa Fluor 594 and Alexa Fluor 488 at the proximity of Ag—Cu alloy nanoparticles.

The invention will improve luminescence sensor design and produce sensors having enhanced signal to noise ratio, resolution and detection sensitivity. An opportunity to enhance the luminescence of sensors will advance a wealth of biomedical and biochemical applications including single molecule detection, DNA sequencing, medical diagnostics, genomics. The improved luminescence will also facilitate fabrication of improved emissive devices, such as lasers or organic light-emitting diodes (OLEDs). Furthermore, this invention will extend the application of MEL to wide range of luminophores applicable for different field ranging from environmental analysis to biological research.

SUMMARY OF THE INVENTION

In our work, we demonstrate metal enhanced luminescence using alloy nanoparticles which offer additional degrees of freedom for tuning their optical properties by altering atomic composition and atomic arrangement. We present a technique for tuning of the optical spectrum by controlling the annealing process for these nanoparticles to achieve extremely large enhancements of luminescence intensity for any luminophore. Some of the new and innovative features of our work are: (1) the use of alloy nanoparticles for luminescence intensity enhancement and (2) the tuning technique of annealing of these particles to achieve extremely large enhancements, and (3) the tailoring of such alloy nanostructure platforms to achieve enhancements in arbitrarily chosen luminophores using nanoparticle composition and annealing schedules as handles.

In one embodiment of the present invention, a method for producing metal alloy nanoparticles to increase metal enhanced luminescence is provided. In the first step, a metallic target is provided. The metallic target is preferably comprised of silver, gold, aluminum, or copper. A metal foil is then attached to the metallic target. The metal foil is preferably selected from silver, gold, aluminum, or copper. Preferably silver is used for the metallic target and copper is used for the metallic foil.

In the next step, at least one metal alloy nanoparticle is deposited on a glass surface. Preferably the at least one metal alloy nanoparticle is deposited through DC magnetron sputtering. The composition of the alloy metal nanoparticles is changed by varying the ratio of the surface area of the target to foil that is exposed to sputtering.

Next, the alloy nanoparticles are annealed. Preferably the annealing temperature is between the ranges of about 298K to about 523K. The annealing time is preferably about 5 minutes. The annealing schedule can be easily changed to acquire the desired surface plasmon resonance spectra.

In a second embodiment of the present invention, a method for increasing metal enhanced luminescence is provided including the steps of: providing a metallic target; attaching a metal foil to the metallic target; depositing metal alloy nanoparticles on a glass surface through sputtering; annealing the alloy nanoparticles; and coating the alloy nanoparticles with a luminophore.

Preferably the annealing temperature is between the ranges of 298 K to about 523 K. Annealing temperature is varied to tune the alloy nanoparticles in the visible and near infrared region of the UV spectrum.

In coating the alloy nanoparticles with the luminophore, it is preferred that the luminophore is positioned at least 5 nm from the metallic core so as to allow for enhanced emissions when exposed to electromagnetic energy. Preferably the luminophore is Alexa Fluor 488 or Alexa Fluor 594.

In a third embodiment of the present invention, a method of increasing metal enhanced luminescence is provided comprising the steps of: providing a silver target; attaching a copper foil to the silver target; depositing metal alloy nanoparticles on a glass surface through DC magnetron sputtering; annealing the alloy nanoparticles; and coating the alloy nanoparticles with a luminophore.

In coating the alloy nanoparticles with the luminophore, it is preferred that the luminophore is positioned about 15 nm from the metallic core so as to allow for enhanced emissions when exposed to electromagnetic energy. Preferably the luminophore is Alexa Fluor 488 or Alexa Fluor 594.

Several fields such as biosensors, single molecule detection, DNA detection, DNA sequencing, quantum cryptography and light emitting diodes (LEDs) will benefit tremendously from luminophore luminescence intensity enhancement, and this technique provides a tunable, simply fabricated, nanostructured platform for such enhancement that can be tailored for any of these applications.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
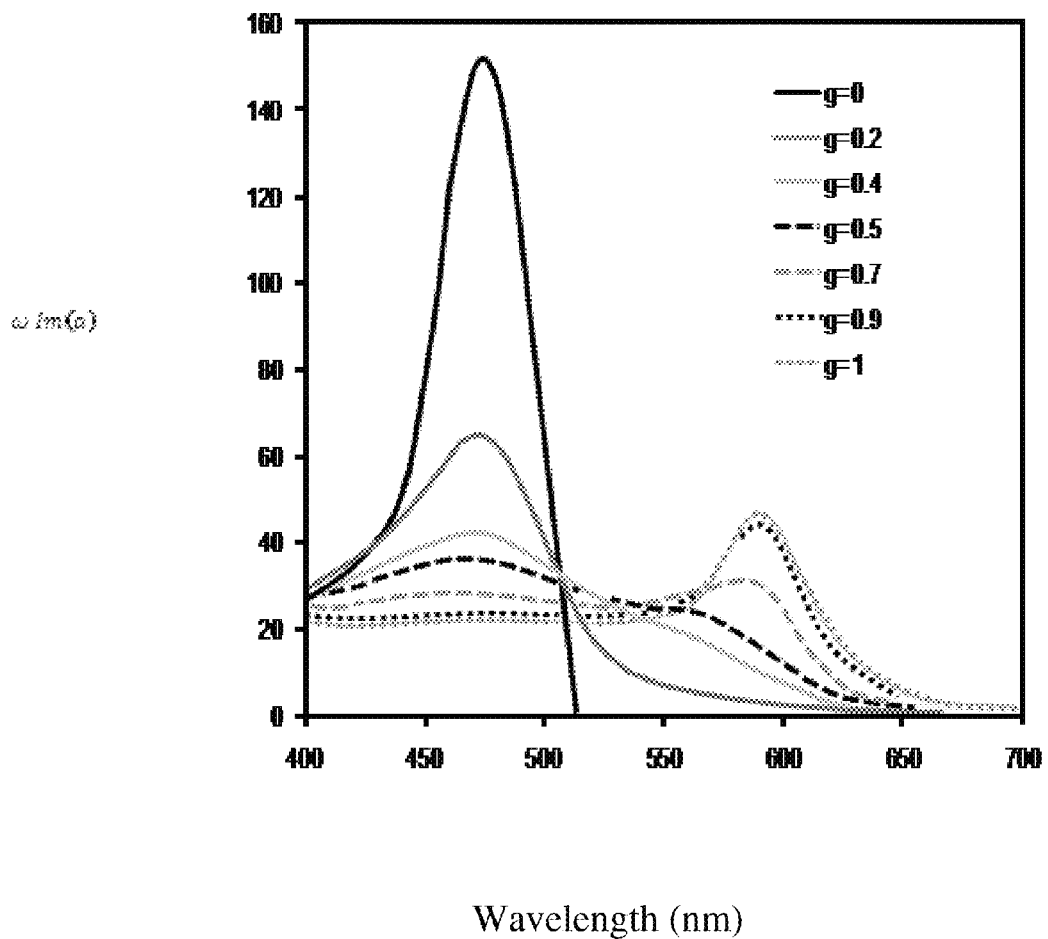
FIG. 1 is a graph showing the calculated extinction spectra for the Ag—Cu core-shell (Ag in core and Cu in shell) materials at different shell layer thickness. Surrounding dielectric media is assumed to be silica glass.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Metal nanoparticles can influence vicinal luminophore molecules in several ways such as by enhancing the incident optical field, increasing the radiative decay rate and quenching the emission by increasing nonradiative decay rate[7, 19-21]. Luminescence enhancement phenomenon is dependent on several parameters. The parameters include material properties, size and shape of nanostructures, and luminophore-nanostructure separation distance.

Distance between luminophore molecules and the nanostructured platform is an important parameter in fluorescence enhancement. If the probe molecules are very close to the nanoparticles (typically less than 5 nm), luminescence emission is quenched due to the Forster transfer of energy from the excited state of the molecule to the surface plasmons of the metal surface. This quenching effect decreases with the cube of separation distance. If the probes are too far (generally more than 20 nm) from the nanoparticle-platform, the influence of the platform is diminished. Hence, there exists an optimum separation distance for maximum emission enhancement[13, 24, 27]. A significant enhancement is seen for a luminophore that is positioned inside and evanescent wave zone of surface plasmon. On the other hand, direct metal-luminophore contact energy transfer quenches fluorescence completely. An ultra-thin transparent dielectric barrier spacer such as SiO2 or polymer with a thickness above 10 nm, between the nanoparticle and the luminophore eliminates quenching and causes significant fluorescence enhancement.

Surface plasmons (electron oscillations on the surface of metals) are easily generated and manipulated using the appropriate metallic nanostructures of having the appropriate size and shape. When a luminophore is in close distance to a metallic nanoparticle which supports the surface plasmons, the luminophore can couple its emission to the surface plasmons. The surface plasmons then radiate the physical properties of the luminophore.

Nanoparticles of the noble metals such as gold and silver have been widely studied thus far given their induced radiative response. However, bi-metallic alloy nanoparticles have great applicability for biological and biochemical applications and have not yet been studied extensively.

The present invention provides for the interactions of luminophores with bi-metallic silver-copper nanoparticles which results in fluorescence enhancement. This system, along with its associated methods, provides significant metal-enhanced luminescence at the vicinity of easily fabricated alloy nanoparticles. These systems offer easy tailoring of optical properties of nanostructured platforms to result in strong luminescence intensity enhancement from different luminophores. Extremely large luminescence enhancements in chosen luminophores can be tailored, as taught herein, through the control of annealing schedules and selection of component metals in the alloy nanoparticles.

"Luminophore" and "fluorophore" are used interchangeably herein to mean any substance that emits electromagnetic energy such as light at a certain wavelength (emission wavelength) when the substance is illuminated by radiation of a different wavelength (excitation wavelength). Both extrinsic and intrinsic luminophores/fluorophores are included herein. Extrinsic luminophores are added covalently or non-covalently to allow molecules that do not normally fluoresce or do not fluoresce at useful levels to be detected. For example, biomolecules such as DNA do not ordinarily fluoresce at detectable levels so extrinsic luminophores are added to DNA to facilitate the detection of DNA on gels. Extrinsic luminophores/fluorophores refer to substances that are luminophores/fluorophores themselves such as those listed in the Molecular Probes Catalogue which is incorporated herein by reference.

Representative fluorophores include but are not limited to Alexa Fluor 488; Alexa Fluor 598; Alexa Fluor 350, Dansyl Chloride (DNS-Cl), 5-(iodoacetamida)fluoroscein (5-IAF); Rhodamine 800 (Rh800), Eu-TDPA [Tris(dibenzoylmethane) mono(5-amino phenanthroline)europium], fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6 G hydrochloride, Lissamine rhodamine B sulfonyl chloride, Texas Redm. sulfonyl chloride, BODIPY™, naphthalamine sulfonic acids including but not limited to 1-anilinonaphthalene-8-sulfonic acid (ANS) and 6-(p-toluidinyl)naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6 naphthyl[vinyl[pyridinium betaine (Naphtyl Styryl), 3,3'dipropylthiadicarbocyanine (diS-C.sub.3-(5)), 4-(p-dipentyl aminostyryl)-1-methylpyridinium (di-5-ASP), Cy-3 lodo Acetamide, Cy-5-N-Hydroxysuccinimide, Cy-7-Isothiocyanate, rhodamine 800, IR-125, Thiazole Orange, Azure B, Nile Blue, A1 Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Intrinsic luminophores/fluorophores include but are not limited to organic compounds that have aromatic ring structures including but not limited to NADH, FAD, tyrosine, tryptophan, purines, pyrimidines, lipids, fatty acids, nucleic acids, nucleotides, neucleosides, amino acids, proteins, peptides, DNA, RNA, sugars, and vitamins.

EXPERIMENTAL PROCEDURES

Synthesis of Silver and Silver-Copper Nanoparticles

Ag or Ag—Cu nanoparticles were deposited on 22×22 mm glass cover slips (Fisher finest cover glass, thickness approximately 140 microns) by using DC magnetron sputtering (Plasma Sciences CRC-100 Sputter Tool). Before the depositions, the cover slips were cleaned by air plasma (Harrick PDC-32G) for 10 minutes at 6.8 watts power setting. During deposition, the background pressure was of the order of $10^{-6}$ Torr, the Ar pressure was 5 mTorr and the current and voltage were 50 mA and 0.4 kV respectively. An Ag target was utilized to deposit the Ag nanoparticles and a Cu foil attached on the Ag target was utilized for the Ag—Cu nanoparticle deposition.

Varying the ratio of the surface area of Ag to Cu exposed for sputtering allowed for changing the composition of the Ag—Cu alloy nanoparticles. Surface morphology of the nanostructures was observed and characterized by transmission electron microscopy (FEI Tecnai F20 S-Twin TEM). An electrical furnace (Lindberg, Blue M) was used for annealing of the Ag—Cu nanoparticles. Annealing temperature ranged from 298 K to 523 K and the annealing time was 5 minutes. Annealing was done in vacuum (30 inch Hg vacuum) to minimize oxidation of the nanoparticles. An UV-vis spectrometer (JASCO, V-530) was used for measuring the light absorption spectra attributed to the SPR of these nanoparticles.

Coating the silver and silver-copper nanoparticle samples with Alexa Fluor 488 and Alexa Fluor 594

Mouse Immunoglobulin G (IgG), labeled with luminophores Alexa Fluor 488 and Alexa Fluor 594 was coated on samples following known methods[23]. Samples were first non-covalently coated with mouse anti-rabbit IgG (Immunopure, Pierce Biotechnology) solution (25 μg/ml) which was diluted with sodium phosphate buffer (pH 7.4). Blocking was performed using blocking solution (1% bovine serum albumin solution in sodium phosphate buffer). Protein labeling kits of both Alexa Fluor 488 and Alexa Fluor 594 were used to label goat anti-mouse IgG with dye. Dye labeled anti-mouse IgG was also diluted using sodium phosphate buffer. Diluted dye-labeled conjugate solution was coated on the sample (already coated with mouse anti-rabbit IgG). As the luminophores were coated following same procedure for all samples, the separation distance between luminophore molecules and nanoparticle platforms are assumed to be the same.

Fluorescence Measurements

The Leica DMI 4000 b inverted fluorescence microscope equipped with Leica DFC340 FX CCD camera was utilized for MEL measurements. This allowed overall inspection of a large area in a single view frame. We took images of each specimen with customized filter sets for each luminophore. Fluorescence microscopy was carried out with a green filter set (Chroma Technology 31001, Exciter D480/30x, Dichroic 505 nm, Emitter D535/40m) for Alexa Fluor 488 and red filter set (Chroma Technology 31004, Exciter D560/40x, Dichroic 595 nm, Emitter D630/60m) for Alexa Fluor 594. To avoid photobleaching, the specimen was exposed to illumination only while taking images. Image Pro-plus version 6 with Scope Pro version 6 (Media Cybernetics, Inc) was used for acquiring and analyzing images. We obtained fluorescence intensities for each sample by analyzing a 1.64 mm×2.19 mm image-section of each substrate. Background images were obtained from an uncoated substrate, and unmodified glass cover slips at the same conditions. Images from the experimental samples were corrected for uneven illumination with the help of these background images. Images of nanoparticle coated glass coverslips were captured and compared with images of bare glass coverslips to test for the possibility of scattered light from metal particles. These images showed that the emission filters effectively removed the scattered light so its contribution is negligible. Luminescence intensity of each sample was determined by measuring the mean intensity and subtracting the mean value of the background image.

Extinction Spectrum Calculation for Core-Shell Material

The extinction coefficient of well dispersed small particles is proportional to $\omega \mathrm{Im}(\alpha)$ where $\alpha$ is the polarizability of the sphere, and $\omega$ is the wavelength of light. $\alpha$ can be calculated from the following equation $$\alpha = R^3 \frac{(\varepsilon_s - \varepsilon_m)(\varepsilon_c + 2\varepsilon_s) + (1-g)(\varepsilon_c - \varepsilon_s)(\varepsilon_m + 2\varepsilon_s)}{(\varepsilon_s + 2\varepsilon_m)(\varepsilon_c + 2\varepsilon_s) + (1-g)(2\varepsilon_s - 2\varepsilon_m)(\varepsilon_c + \varepsilon_s)}$$

where $\in_s$ and $\in_c$ are the dielectric constants of core and shell materials respectively, R is the radius of nanosphere, $\in_m$ is the dielectric constant of medium and g is the volume fraction of shell layer. Based on the above equation, extinction spectra is calculated for 20 nm Ag—Cu core shell nanosphere (FIG. 1).

Computational Methodology

Kümmerlen et al.[19] suggested that the overall quantum efficiency enhancement factor Y (ratio of quantum efficiencies in the presence of metal nanoparticles and without nanoparticles) can be calculated using the following equation:

$$Y = |L(\omega_{abs})|^2 Z(\omega_{flu}) \quad (1)$$

The first term represents the enhancement of local electric field at the excitation frequency ($\omega_{abs}$). The second term describes the change in quantum efficiency due to radiative and non-radiative decay rate enhancements at the emission frequency $\left(\omega_{flu}\right)$. The integrated near-field scattering cross section ($Q_{nf}$) at the excitation wavelength divided by the surface area of the spherical particle is a good measure of average $|L(\omega_{abs})|^2$. Near-field scattering cross section can be calculated using the following equation $$Q_{nf} = 2\frac{r^2}{a^2} \sum_{n=1}^{\infty} \quad (2)$$

$$\{|a_n|^2 [(n+1)|h_{n-1}^{(1)}(ka)|^2 + n|h_{n+1}^{(1)}(ka)|^2] + (2n+1)|b_n|^2|h_n^{(1)}(ka)|^2\}$$

where r is the distance from the center of the spherical nanoparticle and a is the radius of the nanoparticle. $k = \sqrt{\in_m}\omega/c$, $\omega$ is the optical frequency (radian per second), $\in_m$ is the dielectric constant of the media and c is the velocity of light in vacuum. The term $h_n^{(1)}$ is the spherical Henkel function of the first kind. $a_n$ and $b_n$ are well known scattering coefficients.

Using the improved G-N model, we calculated the modifications of the radiative decay rate ($\Gamma_R$) and total decay rate ($\Gamma_{tot}$) of luminophore at the proximity of metal nanoparticles. This model is developed based on the assumption that the sizes of nanoparticles are much smaller than the wavelength. Thus, the retardation effect was accounted for by introducing a correction factor for radiative reaction and dynamic depolarization to modify the quasistatic polarizability of the nanoparticles. This model does not consider multipole radiation and the interference between source dipole and induced dipole is neglected. In this model, the luminophore molecule is modeled as a classical dipole with dipole moment μ. For the radial dipole orientation, the expressions for $\Gamma_R$ and $\Gamma_{tot}$ for the luminophore molecule which is positioned at distance d from the surface of sphere with radius a and dielectric constant $\in = \in' + i\in''$ located in the medium of dielectric constant $\in_m$ is as follows $$\frac{\Gamma_{tot}^\perp}{\Gamma_R^{ref}} = 1 + \frac{3}{4(ka)^3} \sum_l l(l+1)\mathrm{Im}\left\{C_n \frac{\varepsilon - \varepsilon_m}{\varepsilon + \frac{l+1}{l}\varepsilon_m}\left(\frac{a}{a+d}\right)^{2l+4}\right\} \quad (3)$$

$$\frac{\Gamma_R^\perp}{\Gamma_R^{ref}} = \left|1 + 2C_1 \frac{\varepsilon - \varepsilon_m}{\varepsilon + 2\varepsilon_m}\left(\frac{a}{a+d}\right)^3\right|^2 \quad (4)$$

For the tangential dipole orientation, the expressions for $\Gamma_R$ and $\Gamma_{tot}$ are as following $$\frac{\Gamma_{tot}^{//}}{\Gamma_R^{ref}} = 1 + \frac{3}{2(ka)^3} \sum_l (l+1)^2 \mathrm{Im}\left\{C_l \frac{\varepsilon - \varepsilon_m}{\varepsilon + \frac{l+1}{l}\varepsilon_m}\left(\frac{a}{a+d}\right)^{2l+4}\right\} \quad (5)$$

$$\frac{\Gamma_R^{//}}{\Gamma_R^{ref}} = \left|1 - C_l \frac{\varepsilon - \varepsilon_m}{\varepsilon + 2\varepsilon_m}\left(\frac{a}{a+d}\right)^3\right|^2 \quad (6)$$

In the above expressions, l is the angular mode number, and $\Gamma_R^{ref}$ is the radiative decay rate of luminophore in the absence of nanoparticles. $C_1$ is the correction factor for radiation dumping and dynamic depolarization.

$$C_1 = \frac{1}{1 - \frac{ik^3\alpha}{6\pi} - \frac{k^2\alpha}{4\pi a}} \quad (7)$$

$\alpha$ is the quasistatic polarizability.

$$\alpha = 4\pi a^3 \frac{\varepsilon - \varepsilon_m}{\varepsilon + 2\varepsilon_m} \quad (8)$$

For $l \neq 1$, $C_l$ is assumed to be 1.

Dielectric constants for pure Ag and Ag—Cu nanoparticles of 1:1 compositions were taken from the literature.

Figure 2:
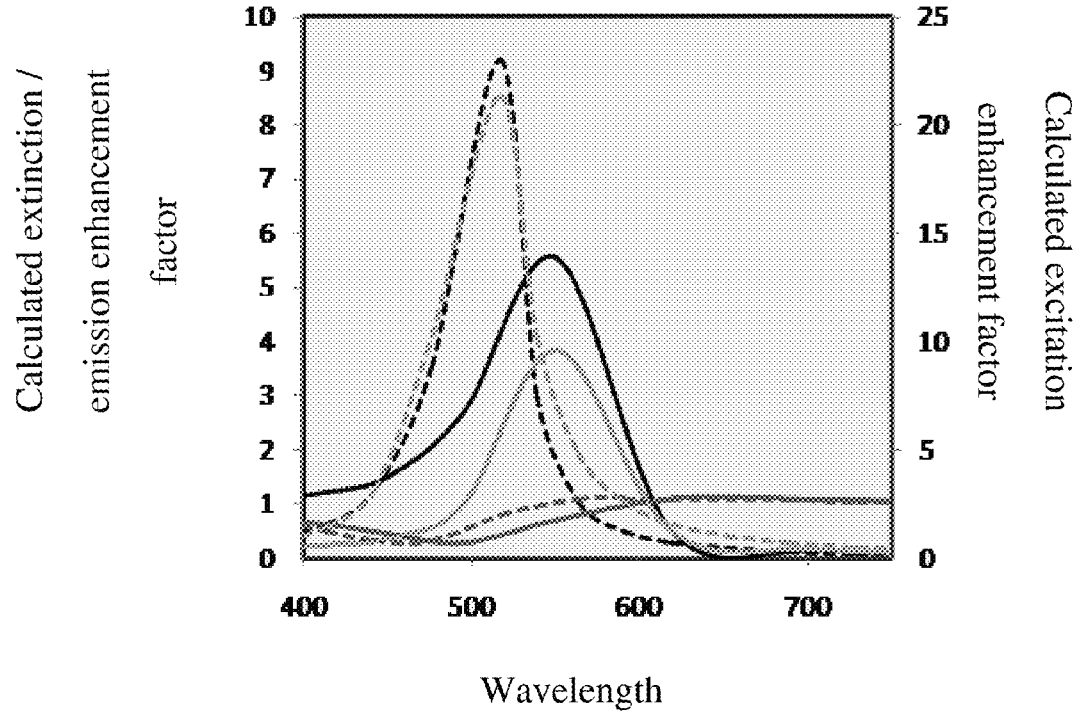
FIG. 2 is a graph showing the theoretically calculated extinction coefficient (black), calculated emission enhancement factor (dark gray) and excitation rate enhancement factor (light gray) for Ag (dotted line) and 1:1 Ag—Cu nanospheres (solid line) (size 20 nm, surrounding dielectric media silica glass, separation distance 15 nm, dipole orientation averaged over all solid angles).

FIG. 2 shows the theoretically calculated extinction coefficient (black), calculated emission enhancement factor (dark gray) and excitation rate enhancement factor (light gray) for Ag (dotted line) and 1:1 Ag—Cu nanospheres (solid line). The size of the nanospheres is 20 nm surrounding dielectric media silica glass. The separation distance is 15 nm and the dipole orientation is averaged over all solid angles.

When a metallic nanoparticle is exposed to an electromagnetic wave, the electrons in the metal (plasmons) oscillate at the same frequency as the incident wave. Subsequently the oscillating electrons radiate electromagnetic radiation at the same frequency as the oscillating electrons. It is this re-radiation of light at the same incident wavelength that is often referred to as Plasmon scatter. The Mie theory for light scattering from large particles can be considered as light radiating from oscillating electric dipoles as well as magnetic dipoles, quadruples and other higher order magnetic multipoles. Scattered light by Mie theory is well known to those with ordinary skill in the art.

Figure 3:
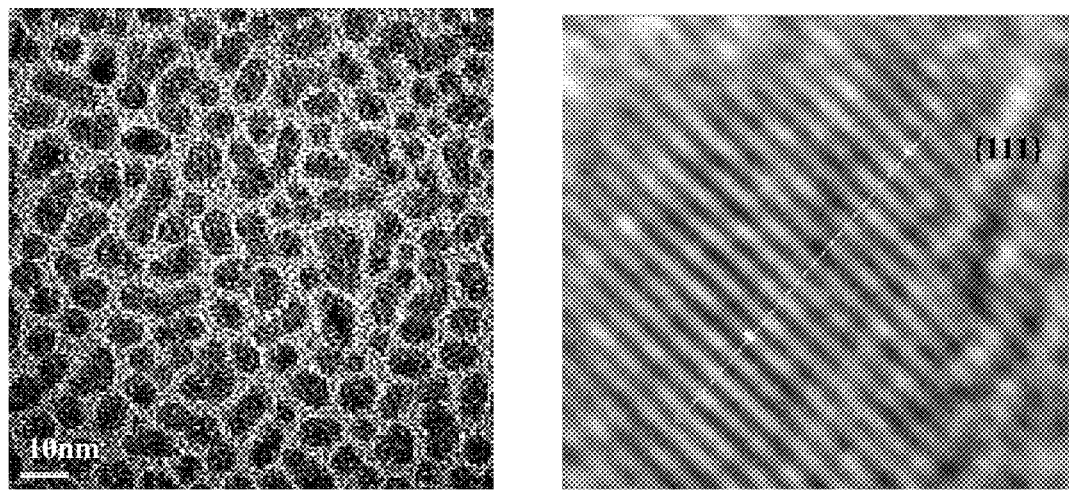
FIG. 3 is a series of images of the Ag—Cu alloy nanoparticles. (A) is a high resolution transmission electron micrograph of the Ag—Cu alloy nanoparticles showing the size of the nanoparticles. (B) is another high resolution transmission electron micrograph of the Ag—Cu alloy nanoparticles showing the lattice spacing. (C) is a graph of the STEM EDS spectra showing that the nanoparticles are comprised of both Ag and Cu.
Figure 3:
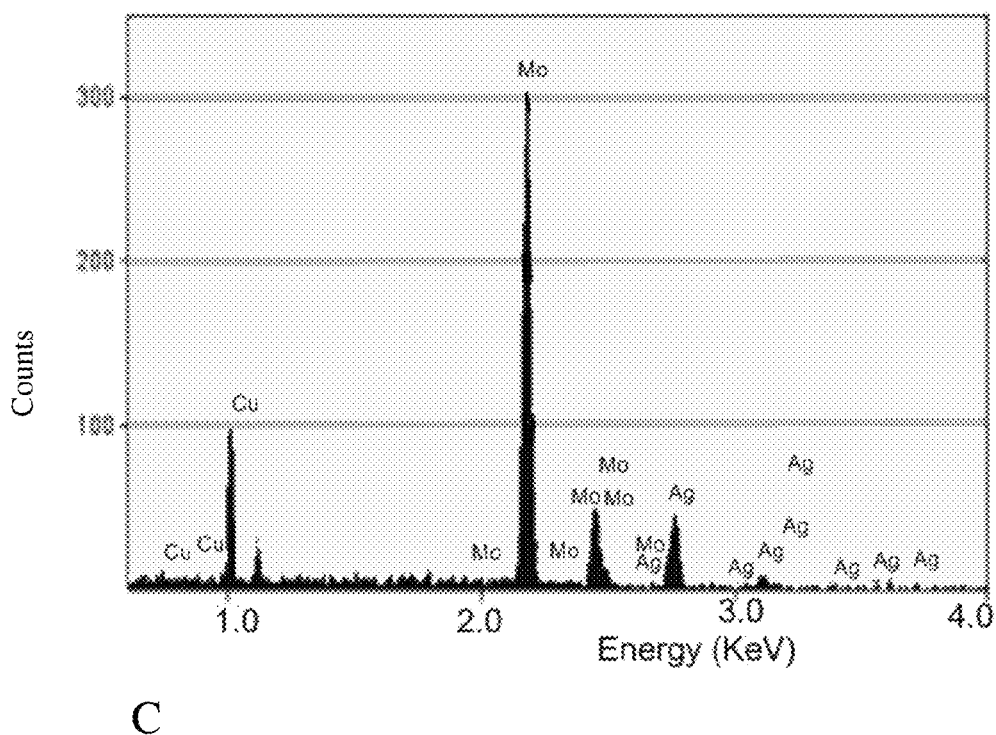

Results:

As shown in FIG. 3A, transmission electron microscopy of the Ag—Cu alloy nanoparticles indicated the average size to be 14.77 nm±5.4 nm (derived from a population of 100 particles). After annealing these nanoparticles at 448 K, the average size is 13.88±4.07 nm. The average size of Ag nanoparticles was 13.78±3.12 nm. From the HRTEM image (FIG. 3B), the lattice spacing was measured to be 0.21-0.24 nm. In the {111} lattice plane, silver has lattice spacing of 0.24 nm whereas the lattice spacing of Cu is 0.21 nm. However, the accuracy of this type of measurement is such that this result alone cannot establish the composition of the nanoparticles. This, combined with STEM EDS data (FIG. 3C), confirms that the nanoparticles are comprised of both Ag and Cu. However Ag—Cu cannot form solid solution at room temperature as Ag—Au. In the Ag—Cu nanoparticles silver and copper remains phase separated. From the STEM EDS data, the approximate composition of the Ag—Cu nanoparticles was found to be 1:1.

Figure 4:
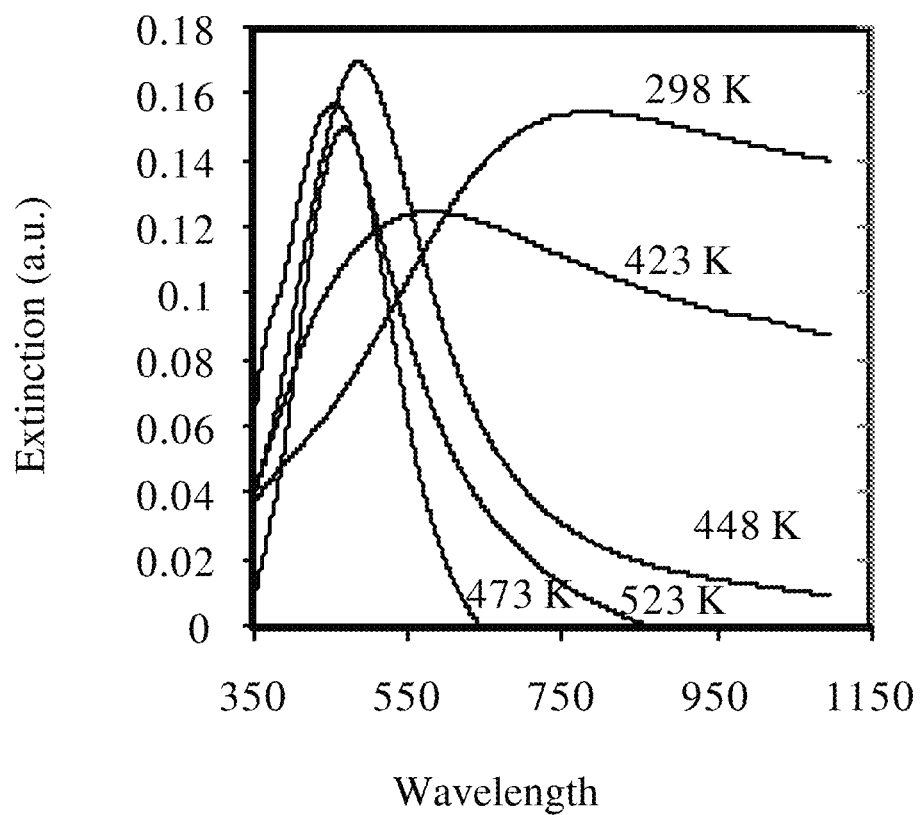
FIG. 4 is a graph of the absorption spectra of annealed Ag—Cu nanoparticles.

The extinction spectra (taken using UV-Vis spectrophotometer, JASCO, V-530) attributed to SPR of Ag—Cu nanoparticles show a single peak in the visible range. With increasing copper percentage, this SPR peak shifts to higher wavelengths and becomes broader (data are not shown here). This result confirms that the nanoparticles are a bimetallic form of silver and copper and not a mixture of silver nanoparticles and copper nanoparticles. The red-shifts of the SPR peaks with increasing copper concentration are attributed to the decrease in conductivity. The SPR peak of Ag—Cu alloy nanoparticles blue-shifts upon increasing the annealing temperature from 298 K to 523 K. With increase in annealing temperature, Cu atoms surface-segregate, thereby increasing the concentration of Ag in the nanoparticle core. As a result, the conductivity of the nanoparticle increases (FIG. 4) and the SPR peak shifts to lower wavelengths, as well as becomes narrower. The SPR peak gradually moves nearer to the SPR peak of pure Ag nanoparticles which can be explained as follows. For the core-shell structure, the effective dielectric constant is a function of the dielectric constant of both core and shell materials as well as the volume fraction of the shell layer. The SPR extinction spectrum peak, which can be calculated from the imaginary part of polarizability, a function of effective dielectric constant, will be nearer to that of core material for shell layer volume fraction up to approximately 0.6.

Figure 5:
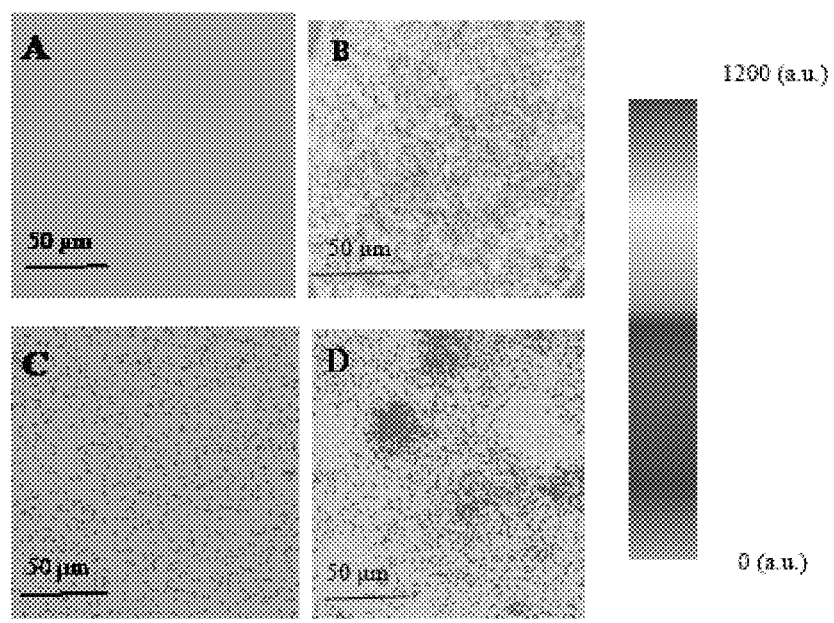
FIG. 5 is an image of luminophores coated on glass and Ag—Cu nanoparticles. (A) Alexa Fluor 488 coated on glass (B) Alexa Fluor 488 coated on 448 K annealed silver-copper alloy nanoparticles (C) Alexa Fluor 594 coated on glass (D) Alexa Fluor 594 coated on room temperature (298 K) silver-copper alloy nanoparticles
Figure 6:
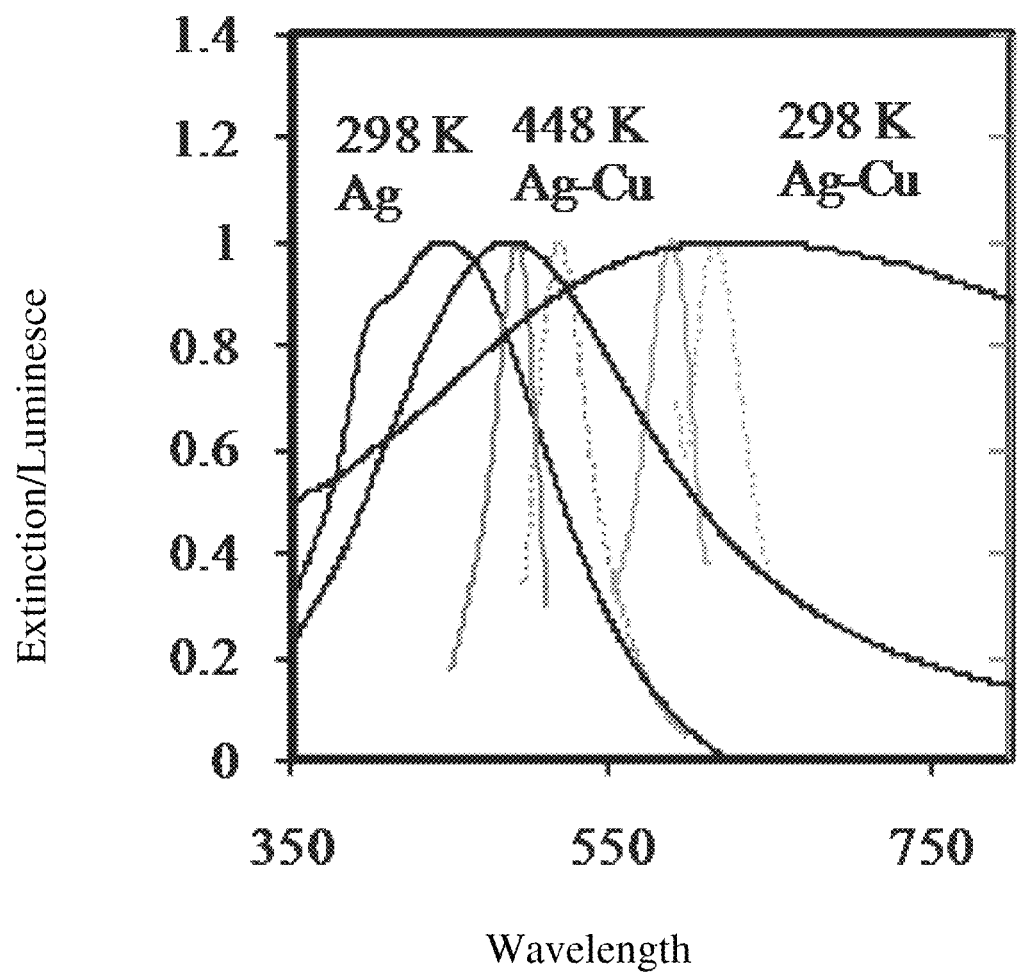
FIG. 6 is a graph showing the extinction spectra of Ag—Cu nanoparticles and Ag nanoparticles used for MEL experiments and absorption and emission spectrum of Alexa Fluor 594 (dotted light gray line is emission spectrum, solid light gray line is excitation spectrum) and Alexa Fluor 488 (dotted dark gray line is emission spectrum, solid dark gray line is excitation spectrum). All spectra were normalized for comparison.

Luminescence of both Alexa Fluor 594 and Alexa Fluor 488 was observed to be enhanced significantly at the vicinity of these Ag—Cu nanoparticles as shown in FIG. 5. Enhancement ratio was calculated by comparing luminescence intensity of the sample with the luminescence intensity of the luminophore coated on an APS coated glass cover slip. As shown in FIG. 6, the SPR spectrum of the 448 K annealed Ag—Cu nanoparticles nicely overlaps both the excitation and emission spectra of Alexa Fluor 488. This annealed Ag—Cu nanoparticle platform results in very strong enhancement (141.48±19.20 times) of luminescence of Alexa Fluor 488. The Ag—Cu nanoparticles at 298 K, which show less spectral overlap, also result in large enhancement (100.87±10.21 times). The lowest enhancement (50.22±10.80) was observed at the proximity of pure Ag nanoparticles (deposited at the same conditions as Ag—Cu nanoparticles), where the spectral overlap is least.

The effect of spectral overlap on luminescence enhancement is also pronounced for Alexafluor 594. We found 23.91±12.37 times enhancement of emission from Alexa Fluor 594 at the proximity of room temperature grown Ag—Cu nanoparticles. On the other hand, both pure Ag nanoparticles and the 448 K annealed Ag—Cu nanoparticles grown at similar conditions result in lower enhancement (9.74±0.9 times for 448 K annealed Ag—Cu nanoparticles and 6.89±3.06 times for Ag particles) because of less spectral overlap. The best case Ag—Cu studied was 2.8 times better than pure Ag for Alexafluor 488 and 3.5 times better for Alexafluor 594. In both cases, the spectral overlap was largest when maximum enhancement was seen. It is possible to achieve this enhancement only for the alloy particles because the breadth of the peak can also be tuned.

By enhancing the local field for absorption and/or quantum yield due to radiative and non radiative decay rates, we can increase the intensity of luminescence. The intensity of the incident optical wave is enhanced in the near field of the nanoparticles at the SPR wavelength. Hence, strongest excitation is observed when the SPR spectrum of nanoparticles overlaps the excitation peak of the luminophore[9]. Same as for excitation, when SPR spectrum of the nanoparticles overlaps the emission spectrum of luminophore, emission intensity enhancement is the highest[26]. However, as in this case high quantum yield luminophores were used, excitation enhancement is more pronounced than emission enhancement. As a result, the spectral overlap with excitation spectra is more important.

Here, we present a theoretical calculation for overall quantum efficiency factors in the proximity of pure Ag nanoparticles and for the 1:1 Ag—Cu nanoparticles, based on the model suggested by Kümmerlen et al.[19] which includes both excitation and emission enhancement factors (detailed computational methodology is given in the supplementary information). Kümmerlen et al.[19] suggested integrated near-field scattering cross section ($Q_{nf}$) at the excitation wavelength divided by the surface area of the spherical particle is a good measure of the average excitation enhancement factor. The corrected G-N model was used to calculate the quantum efficiency change due to radiative and nonradiative decay rate enhancements. Exact representation of experimental conditions is not possible in theoretical calculations due to the differences in experimental geometry (nanoparticles are not in a homogeneous dielectric environment, all the nanoparticles are not of spherical shape and not of the same size, luminophore-nanostructures separation distance is not uniformly the same). Furthermore, accurate dielectric constants of room temperature and annealed Ag—Cu nanoparticles are not known, or evaluable, as they remain phase separated.

However, these calculations provide some insights into the experimental findings. FIG. 2 shows the theoretically calculated extinction coefficient (using Mie theory), and the overall quantum efficiency enhancement factor for pure Ag and 1:1 bimetallic Ag—Cu nanoparticles. From FIG. 2, the effect of spectral overlap is clearly evident. In the wavelength range of 450 nm to 555 nm, as the extinction spectrum for the Ag nanoparticles is more pronounced, overall quantum efficiency enhancement in the proximity of the Ag is better than that of the Ag—Cu nanoparticles. Most importantly, in the wavelength range of 550 nm to 625 nm, the Ag—Cu nanoparticles show better overall quantum efficiency enhancement than pure Ag as the spectral overlap is better for the Ag—Cu nanoparticles. For both Ag nanoparticles and Ag—Cu nanoparticles, the maximum overall quantum efficiency enhancement wavelengths are slightly red-shifted with respect to the extinction coefficient peaks. As the calculations were done for the high quantum yield (0.5) luminophore, the excitation enhancement effect is more pronounced than the emission enhancement effect. These theoretical findings help in interpreting our experimental observations.

In regard to the MEL effect of Ag—Cu alloy nanoparticles it was found that Ag—Cu alloy nanoparticle platform produce strong enhancement for the two luminophores studied, viz. Alexa Fluor 488 and Alexa Fluor 594. We developed a synthesis technique to tune the SPR spectrum of alloy nanoparticles from infrared to visible region very easily by changing composition or annealing schedule. Ag—Cu alloy nanoparticles were observed to show even better enhancement than pure Ag nanoparticles when the SPR spectrum was tuned to result in maximum spectral overlap. For a particular luminophore, we can tune the annealing temperature of particular composition Ag—Cu nanoparticles to result in maximum spectral overlap which can help in optimum luminescence enhancement.

SPR wavelengths of these Ag—Cu nanoparticles were tuned in the visible and near infrared region by changing only one experimental condition, annealing temperature. We observed strong emission enhancement of luminophores (141.48±19.20 times for Alexa Fluor 488 and 23.91±12.37 times for Alexa Fluor 594) at the vicinity of Ag—Cu nanoparticles when SPR spectrum was tuned to produce maximum spectral overlap. This platform can be effectively used to enhance luminescence of different luminophores since the SPR spectrum of Ag—Cu alloy nanoparticles is easily tailored. This finding opens a new avenue for the utilization of metal alloy nanoparticles in MEL applications.

REFERENCES

The content of all references cited herein are incorporated by reference herein for all purposes.

1. Azoulay, A. Débarre, A. Richard, P. Tchénio, and (2000). Europhys. Lett. 51, 374 (2000).
2. K. Aslan, J. R. Lakowicz, and C. D. Geddes, Anal. Chem. 77, 2007 (2005).
3. K. Aslan, J. R. Lakowicz, and C. D. Geddes, Anal. Bioanal. Chem. 382, 926 (2005).
4. K. Aslan, J. R. Lakowicz, H. Szmacinski, and C. D. Geddes, J. Fluoresc. 15, 37 (2005).
5. K. Aslan, Z. Leonenko, J. R. Lakowicz, and C. D. Geddes, J. Phys. Chem. B 109, 3157 (2005).
6. K. Aslan, Meng Wu, J. R. Lakowicz, and C. D. Geddes, J. Am. Chem. Soc. 129, 1524 (2007).
7. M. H. Chowdhury, K. Aslan, S, N. Malyn, J. R. Lakowicz, and C. D. Geddes, J. Fluoresc. 16, 295-299 (2006).
8. C. D. Geddes, H. Cao, I. Gryczynski, Z. Gryczynski, J. Fang, and J. R. Lakowicz, J. Phys. Chem. A 107, 3443 (2003).
9. C. D. Geddes and J. R. Lakowicz, J. Fluoresc. 12, 121 (2002).
10. C. D. Geddes, A. Parfenov, and J. R Lakowicz, Appl. Spectrosc. 57, 526 (2003).
11. J R Lakowicz, J. Malicka, I. Gryczynski, Z. Gryczynski, and C. D. Geddes, J. Phys. D: Appl. Phys. 36, R240-R249 (2003).
12. K. Ray, R. Badugu, and J. R Lakowicz, J. Am. Chem. Soc. 128, 8998 (2006).
13. K. Ray, R. Badugu, and J. R Lakowicz, Langmuir 22, 8374 (2006).
14. K. Ray, R. Badugu, and J. R Lakowicz, J. Phys. Chem. B 110, 13499 (2006)
15. J. Zhang, Y. Fu, and J R Lakowicz, J. Phys. Chem. C 111,1955 (2007).
16. J. Zhang, E. Matveeva, I. Gryczynski, Z. Leonenko, and J. R Lakowicz, J. Phys. Chem. B 109, 7969 (2005).
17. Y. Zhang, K. Aslan, M. J. R. Previte, and C. D. Geddes, Appl. Phys. Lett. 90, 173116 (2007).
18. C. D. Geddes, A. Parfenov, D. Roll, I. Gryczynski, J. Malicka, and J. R. Lakowicz, J. Fluoresc. 13, 267 (2003).
19. J. Kümmerlen, A. Leitner, H. A Brunner, F. R. A Aussenegg, and A. A Wokaun, Mol. Phys. 80, 1031 (1993).
20. J. R. Lakowicz, Y. Shen, S. D'Auria, J. Malicka, J. Fang, Z. Gryczynski, and I. Gryczynski, Anal. Biochem. 301, 261 (2002).
21. J. Malicka, I. Gryczynski, Z. Gryczynski, and J. R Lakowicz, Anal. Biochem. 315, 57 (2003).
22. F. Tam, G. P. Goodrich, B. R. Johnson, and N.J. Halas, Nano Lett. (2007).
23. P. J. Tarcha, J. Desaja-Gonzalez, S. Rodriguez-Llorente, and R. Aroca, Appl. Spectrosc. 53, 43 (1999).
24. K. Aslan, S, N. Malyn, and C. D. Geddes, J. Fluoresc. 17, 7 (2007).
25. P. P. Pompa, L. Martiradonna, A. D. Torre, F. D. Sala, L. Manna, M. D. Vittorio, F. Calabi, R. Cingolani, and R. Rinaldi, Nat. Nanotechnol. 1 (2006).
26. K. Ray, M. H. Chowdhury, and J R Lakowicz, Anal. Chem. 79, 6480 (2007).
27. Y. Chen, K. Munechika, and D. S. Ginger, Nano Lett. 7, 690 (2007).
28. M. Thomas, J.-J. Greffet, and R. Carminati, Appl. Phys. Lett. 85, 3863 (2004).
29. J. Zhang, H. Liu, Z. Wang, and N. Ming, J. Solid State Chem. 180, 1291 (2007).
30. J. Song, H. Li, J. Li, S. Wang, and S. Zhou, Appl. Opt. 41, 5413 (2002).
31. M. Hirai and A. Kumar, J. Appl. Phys. 100, 014309 (2006).
32. M. Hirai and A. Kumar, Journal of Electronic Materials 36, 1574 (2007).
33. S. Link, Z. L. Wang, and M. A. El-Sayed, J. Phys. Chem. B 103, 3529 (1999).
34. M. Moskovits, I. S.-S. loufová, and B. Vlčková, Journal of Chemical Physics 116, 10435 (2002).
35. A. Pal, S. Shah, and S. Devi, Colloids and Surfaces A: Physicochemical and Engineering Aspects 302, 483 (2007).
36. J. Zhu, Physica E: Low-dimensional Systems and Nanostructures 27, 296 (2005).
37. E. Matveeva, Z. Gryczynski, J. Malicka, I. Gryczynski, and J. R Lakowicz, Anal. Biochem. 334, 303 (2004).
38. J. Zhang, H. Liu, Z. Wang, and N. Ming, J. Solid State Chem. 180, 1291 (2007).
39. A. Sharma, G. Mohr, J. Phys. D: Appl. Phys. 41, 055106 (2008).
40. S. Zynio, A. Samoylov, E. Surovtseva, V. Mirsky, Y. Shirshov, Sensors 2, 62 (2002).
41. E. Dulkeith, M. Ringler, T. A. Klar, J. Feldmann, A. MunozJavier, W. J. Parak, Nano Lett. 5, 585 (2005)

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of enhancing the fluorescence of luminophores comprising:

providing bimetallic nanoparticles wherein the nanoparticles form a platform;
determining surface plasmon resonance (SPR) spectrum of the nanoparticle platform;
modifying the atomic composition of the bimetallic nanoparticles to change peak position and width of the SPR spectrum;
modifying the atomic arrangement of the bimetallic nanoparticles to change peak position and width of the SPR spectrum;
providing luminophores wherein the luminophores are positioned at a predetermined distance from the nanoparticles;
determining emission spectrum of the luminophores;
determining absorption spectrum of the luminophores; and
calculating an overall quantum efficiency factor for the luminophores using emission enhancement factors and excitation rate enhancement factors to determine a specific level of enhancement for the luminophores;
wherein the atomic composition and the atomic arrangement of the nanoparticles are modified to provide spectral overlap between the SPR spectrum of the nanoparticle platform and the emission and the absorption spectra of the luminophores;
whereby the maximum spectral overlap results in enhanced luminescence.

2. The method of claim 1, wherein the luminophores are positioned between about 5 nm and about 20 nm from the nanoparticles.

3. The method of claim 1, wherein the bimetallic nanoparticles are comprised of a combination of at least two metals selected from the group consisting of gold, silver, aluminum and copper.

4. The method of claim 1, wherein the bimetallic nanoparticles are a combination of silver and copper.

5. The method of claim 1, wherein the atomic composition is modified by varying a ratio of surface area of a first metal with respect to a second metal in a bimetallic target in a sputtering process.

6. The method of claim 1, wherein the atomic arrangement is modified by changing annealing temperature.

7. The method of claim 6, wherein the annealing temperature is increased.

8. A method of enhancing the fluorescence of luminophores comprising:
providing bimetallic nanoparticles wherein the nanoparticles form a platform;
determining surface plasmon resonance (SPR) spectrum of the nanoparticles;
providing luminophores wherein the luminophores are positioned at a predetermined distance from the nanoparticle platform;
determining emission spectrum of the luminophores;
determining absorption spectrum of the luminophores;
modifying the SPR spectrum of the nanoparticles to provide spectral overlap between the SPR spectrum of the nanoparticles and the emission and the absorption spectra of the luminophores; and
calculating an overall quantum efficiency factor for the luminophores using emission enhancement factors and excitation rate enhancement factors to determine a specific level of enhancement for the luminophores;
whereby the spectral overlap results in enhanced luminescence.

9. The method of claim 8, wherein the SPR spectrum of the nanoparticles is modified by modifying the atomic composition of the bimetallic nanoparticles.

10. The method of claim 9, wherein the atomic composition is modified by varying a ratio of surface area of a first metal with respect to a second metal in a bimetallic target in a sputtering process.

11. The method of claim 8, wherein the SPR spectrum of the nanoparticles is modified by modifying the atomic arrangement of the bimetallic nanoparticles.

12. The method of claim 11, wherein the atomic arrangement is modified by changing annealing temperature.

13. The method of claim 8, wherein the bimetallic nanoparticles are comprised of a combination of at least two metals selected from the group consisting of gold, silver, aluminum and copper.

14. The method of claim 8, wherein the bimetallic nanoparticles are a combination of silver and copper.

15. The method of claim 8, wherein the luminophores are positioned between about 5 nm and about 20 nm from the nanoparticle platform.

* * * * *